(12) United States Patent
Hashimoto et al.

(10) Patent No.: US 8,906,151 B2
(45) Date of Patent: Dec. 9, 2014

(54) CALCIUM PHOSPHATE COMPOSITION AND PROCESS FOR PRODUCING THE SAME

(75) Inventors: Tadashi Hashimoto, Okayama (JP); Takahiro Sekiguchi, Okayama (JP); Koichi Okada, Kurashiki (JP)

(73) Assignee: Kuraray Noritake Dental Inc., Kurashiki-shi (JP)

( * ) Notice: Subject to any disclaimer, the term of this patent is extended or adjusted under 35 U.S.C. 154(b) by 371 days.

(21) Appl. No.: 12/160,971

(22) PCT Filed: Jan. 15, 2007

(86) PCT No.: PCT/JP2007/050432
§ 371 (c)(1), (2), (4) Date: Jul. 15, 2008

(87) PCT Pub. No.: WO2007/083601
PCT Pub. Date: Jul. 26, 2007

(65) Prior Publication Data
US 2010/0236449 A1 Sep. 23, 2010

(30) Foreign Application Priority Data
Jan. 16, 2006 (JP) ................................ 2006-008078

(51) Int. Cl.
| | | |
|---|---|---|
| A61L 24/02 | (2006.01) | |
| A61L 27/42 | (2006.01) | |
| A61K 6/033 | (2006.01) | |
| A61L 24/00 | (2006.01) | |
| C04B 28/34 | (2006.01) | |
| A61K 6/00 | (2006.01) | |
| A61K 6/02 | (2006.01) | |
| A61K 6/06 | (2006.01) | |
| C04B 111/00 | (2006.01) | |

(52) U.S. Cl.
CPC .............. *A61L 27/425* (2013.01); *A61K 6/033* (2013.01); *A61L 24/0063* (2013.01); *C04B 28/344* (2013.01); *A61K 6/0008* (2013.01); *A61K 6/0067* (2013.01); *A61K 6/0215* (2013.01); *A61K 6/024* (2013.01); *A61K 6/0245* (2013.01); *A61K 6/025* (2013.01); *A61K 6/0255* (2013.01); *A61K 6/0643* (2013.01); *C04B 2111/00836* (2013.01)
USPC .......................................... 106/35; 106/691

(58) Field of Classification Search
None
See application file for complete search history.

(56) References Cited

U.S. PATENT DOCUMENTS

| | | | | |
|---|---|---|---|---|
| 5,092,888 A | * | 3/1992 | Iwamoto et al. | 623/23.58 |
| 5,993,535 A | * | 11/1999 | Sawamura et al. | 106/691 |

FOREIGN PATENT DOCUMENTS

| | | |
|---|---|---|
| JP | 1 176252 | 7/1989 |
| JP | 1-176252 | 7/1989 |
| JP | 2 307845 | 12/1990 |
| JP | 7 267617 | 10/1995 |
| JP | 11 130491 | 5/1999 |
| JP | 3017536 | 3/2000 |

OTHER PUBLICATIONS

Gbureck, improvement of mechanical properties of self setting calcium phosphate bone cements mixed with different metal oxides, 2003, werkstofftech, 34, No. 12, pp. 1036-1040.*
Mitchell et al, interaction of silica fume with calcium hydroxide solutions and hydrated cement pastes, 1998, cement and concrete research, vol. 28, No. 11, pp. 1571-1584.*
Chung, improving cement based materials by silica fume, 2001, crc press llc, Applied Materials Science.*
Takahashi et al, preparation and compressive strength of tricalcium phosphate based cement dispersed with ceramic particles, 2004, ceramics international, vol. 30, pp. 199-203.*
Sugawara, Akiyoshi et al., "Histopathological Reaction of a Calcium Phosphate Cement Root Canal Filler", Journal of Hard Tissue Biology, vol. 4, No. 1, pp. 1-7 (1995).
U.S. Appl. No. 13/857,801, filed Apr. 5, 2013, Hashimoto et al.

* cited by examiner

*Primary Examiner* — Melvin C Mayes
*Assistant Examiner* — Stefanie Cohen
(74) *Attorney, Agent, or Firm* — Oblon, Spivak, McClelland, Maier & Neustadt, L.L.P.

(57) ABSTRACT

A calcium phosphate composition comprising tetracalcium phosphate particles (A), calcium hydrogen phosphate particles (B) and at least one kind of inorganic particles (C) selected from silica particles or titania particles, wherein the mixing ratio (A/B) of (A) to (B) is from 45/55 to 55/45 in molar ratio, the inorganic particles (C) have an average particle diameter of from 0.002 to 0.5 μm, and the inorganic particles (C) are contained in an amount of 0.1 to 20 parts by weight based on 100 parts by weight of (A) and (B) in total. Thereby provided is a calcium phosphate composition such that when it is used as a material for bone repair, a formed bone has high mechanical strength and a high bone replacement rate is achieved.

9 Claims, No Drawings

CALCIUM PHOSPHATE COMPOSITION AND PROCESS FOR PRODUCING THE SAME

TECHNICAL FIELD

The present invention relates to calcium phosphate compositions. In particular, it relates to a calcium phosphate composition containing tetracalcium phosphate particles, calcium hydrogen phosphate particles and at least one kind of inorganic particles selected from silica particles or titania particles, and to a method for producing the same.

BACKGROUND ART

Hydroxyapatite ($Ca_{10}(PO_4)_6(OH)_2$), which is obtained by sintering a calcium phosphate composition, has a composition close to inorganic components of bones and teeth and has a bioactivity, which is a property of bonding directly to bones. Therefore, its use as a material for repairing bone defects or bone voids has been reported. When a bone defector a bone void is filled up with a material made of such hydroxyapatite obtained by sintering, it can be connected directly to the bone, but it has been reported that bone formation due to remodeling of the bone fails to occur. Therefore, it is reported that hydroxyapatite obtained by sintering a calcium phosphate composition only plays a role of a space-making material which only exists as it is and that it is difficult to have a bone forming ability even if it stays inside the body for a long period of time.

On the other hand, it is known that among calcium phosphate compositions, a cement type of composition, that is, a calcium phosphate composition having setting property is converted gradually to living body-absorbable hydroxyapatite in a living body or in an oral cavity and moreover it can integrate with a biological hard tissue while maintaining its form. Such a calcium phosphate composition is not only superior in biocompatibility but also has formability, and it is replaced with bone itself by the bone formation originating at absorption of osteoclasts. Therefore, its application as a medical and dental material is expected.

For example, Japanese Patent No. 3017536 (patent document 1) discloses that a mixture of tetracalcium phosphate and anhydrous calcium hydrogen phosphate reacts in the presence of water to form hydroxyapatite. It is reported that when the hydroxyapatite comes into contact with a biological hard tissue, it can replace bone gradually. However, the resulting hydroxyapatite does not necessarily have good mechanical strength, and it was sometimes difficult to be applied to a site where a load is to be added. In addition, the rate of its replacement with bone is also insufficient. Therefore, further improvement has been desired.

Non-patent document 1 discloses that a calcium phosphate cement made of tetracalcium phosphate and anhydrous calcium hydrogen phosphate exhibits good filling ability and it has high compatibility with the periapical tissues when used as a root canal filler. Cases where zirconia was used as a radiopaque material are also disclosed. However, a hardened calcium phosphate cement obtained by setting such a calcium phosphate cement does not necessarily have satisfactory mechanical strength, and therefore an improvement has been desired.

Patent document 1: Japanese Patent No. 3017536
Non-patent document 1: Akiyoshi Sugawara et al., "Histopathological Reaction of a Calcium Phosphate Cement Root Canal Filler", Journal of Hard Tissue Biology, 4 (1): p 1-7, 1995

DISCLOSURE OF THE INVENTION

Problems to be Solved by the Invention

The present invention was made in order to solve the above-described problems. An object thereof is to provide a calcium phosphate composition such that when it is used as a material for bone repair, a formed bone has high mechanical strength and a high bone replacement rate is achieved, and to provide a method for producing the same. Further, an object thereof is also to provide a suitable method for producing such a calcium phosphate composition and to provide suitable application of such a calcium phosphate composition.

Means for Solving the Problems

The above-mentioned problems are solved by providing a calcium phosphate composition comprising tetracalcium phosphate particles (A), calcium hydrogen phosphate particles (B) and at least one kind of inorganic particles (C) selected from silica particles or titania particles, wherein the mixing ratio (A/B) of (A) to (B) is from 45/55 to 55/45 in molar ratio, the inorganic particles (C) have an average particle diameter of from 0.002 to 0.5 μm, and the inorganic particles (C) are contained in an amount of 0.1 to 20 parts by weight based on 100 parts by weight of (A) and (B) in total.

In this embodiment, it is preferable that the tetracalcium phosphate particles (A) have an average particle diameter of from 5 to 30 μm. It is also preferable that the calcium hydrogen phosphate particles (B) have an average particle diameter of from 0.1 to 5 μm. Such a calcium phosphate composition is, in a preferred embodiment, a composition for medical use and particularly it is suitable as a bone cement.

The above-mentioned problems are also solved by providing a method for producing a calcium phosphate composition paste comprising tetracalcium phosphate particles (A), calcium hydrogen phosphate particles (B) and at least one kind of inorganic particles (C) selected from silica particles or titania particles, wherein water is added to a powder of a calcium phosphate composition in which the mixing ratio (A/B) of (A) to (B) is from 45/55 to 55/45 in molar ratio, the inorganic particles (C) have an average particle diameter of from 0.002 to 0.5 μm, and the inorganic particles (C) are contained in an amount of 0.1 to 20 parts by weight based on 100 parts by weight of (A) and (B) in total; and then kneading is performed. The above-mentioned problems are also solved by providing a method for producing a calcium phosphate composition paste comprising tetracalcium phosphate particles (A), calcium hydrogen phosphate particles (B) and at least one kind of inorganic particles (C) selected from silica particles or titania particles, wherein an aqueous dispersion, in which the inorganic particles (C) have an average particle diameter of from 0.002 to 0.5 μm and the inorganic particles (C) are contained in an amount of 0.1 to 20 parts by weight based on 100 parts by weight of (A) and (B) in total, is added to a powder of a composition comprising the tetracalcium phosphate particles (A) and the calcium hydrogen phosphate particles (B) in which the mixing ratio (A/B) of (A) to (B) is from 45/55 to 55/45 in molar ratio; and then kneading is performed.

Effect of the Invention

When the calcium phosphate composition of the present invention is used as a material for bone repair, or the like, a bone formed therefrom has high mechanical strength, and a high bone replacement rate is achieved. Therefore, it is suitable as a material for medical use and dental use.

BEST MODE FOR CARRYING OUT THE INVENTION

The calcium phosphate composition of the present invention is comprised of tetracalcium phosphate particles (A), calcium hydrogen phosphate particles (B) and at least one kind of inorganic particles (C) selected from silica particles or titania particles.

When a calcium phosphate composition containing tetracalcium phosphate particles (A) and calcium hydrogen phosphate particles (B) is kneaded in the presence of water, it forms thermodynamically stable hydroxyapatite and sets. At this time, it has become clear that, by containing at least one kind of inorganic particles (C) selected from silica particle or titania particles in addition to tetracalcium phosphate particles (A) and calcium hydrogen phosphate particles (B), the bone replacement rate of the hydroxyapatite formed in a site where the calcium phosphate composition has been filled is improved, and the mechanical strength of bone formed after implantation is improved. While the reason for this is not necessarily clear, the following mechanism is presumed.

First, when tetracalcium phosphate particles (A) and calcium hydrogen phosphate particles (B) come into contact with water, the tetracalcium phosphate particles (A) and the calcium hydrogen phosphate particles (B) partly dissolve in water. Then, when both the materials react together at the site where they have dissolved, hydroxyapatite crystals form. The pH of the aqueous solution in this process is preferably a singular point (pH 8.5-9) where the solubility curves of both the materials cross each other because hydroxyapatite crystals are formed there most smoothly. It seems that when at least one kind of many fine inorganic particles (C) selected from silica particles or titania particles are present, the inorganic particles (C) serve as a nucleating agent and, as a result, many hydroxyapatite crystals form at once. It also seems that smaller hydroxyapatite crystals are formed in comparison to the case of containing no inorganic particles (C). Such fine hydroxyapatite crystals are preferable for remodeling of osteoblasts, and they are expected to be replaced with autologous bone quickly.

The production method of the tetracalcium phosphate [$Ca_4(PO_4)_2O$] particles (A) to be used in the present invention is not particularly restricted. Commercially available tetracalcium phosphate particles may be used as it is, or alternatively, they may be used after appropriate regulation of their particle size by grinding. As a grinding method, a method same as the grinding method of calcium hydrogen phosphate particles (B) described below may be used.

It is preferable that the tetracalcium phosphate particles (A) have an average particle diameter of from 5 to When the average particle diameter is less than 5 μm, tetracalcium phosphate particles (A) dissolve excessively and the pH of the aqueous solution becomes so high that hydroxyapatite does not form smoothly and the mechanical strength of a set product may deteriorate. The average particle diameter is more preferably 8 μm or more. On the other hand, when the average particle diameter is greater than 30 μm, a paste obtained by mixing with a liquid material composed mainly of water does not show a sufficiently high viscosity, or a rougher feeling is caused; that is, the paste properties are not good. In use as a root canal filler or the like for dental use, when it is injected to a narrow implantation site with a syringe, the tip of a nozzle may be clogged therewith. The average particle diameter is more preferably 20 μm or less. The average particle diameter of the tetracalcium phosphate particles (A) to be used in the present invention is calculated through measurement using a laser diffraction type particle size distribution analyzer.

While the calcium hydrogen phosphate particles (B) to be used in the present invention may be either an anhydride [$CaHPO_4$] or a dihydrate [$CaHPO_4.2H_2O$], the anhydride is preferably used. It is preferable that the calcium hydrogen phosphate particles (B) have an average particle diameter of from 0.1 to 5 μm. When the average particle diameter is less than 0.1 μm, the viscosity of a paste obtained by mixing with a liquid material may become excessively high. It is more preferably 0.5 μm or more. On the other hand, when the average particle diameter is greater than 5 μm, the calcium hydrogen phosphate particles (B) become hardly soluble in a liquid material. Therefore, tetracalcium phosphate particles (A) dissolve excessively and the pH of the aqueous solution becomes so high that hydroxyapatite does not deposit smoothly and the mechanical strength of a set product may deteriorate. The average particle diameter is more preferably 2 μm or less. The average particle diameter of the calcium hydrogen phosphate particles (B) is calculated in the same manner as the average particle diameter of the tetracalcium phosphate particles (A).

The production method of calcium hydrogen phosphate particles (B) having such an average particle diameter is not particularly restricted. While commercial products may be used if available, it is often preferable to grind a commercially available product. In such a case, a grinding machine, such as a ball mill, a pestle and mortar machine and a jet mill, can be used. Calcium hydrogen phosphate particles (B) can be obtained also by grinding a raw material powder of calcium hydrogen phosphate together with a liquid agent such as alcohol by use of a pestle and mortar machine, a ball mill, or the like to prepare a slurry, and drying the obtaining slurry. As the grinding machine in this process, a ball mill is preferably used. As the material of its pot and balls, alumina or zirconia is preferably used.

As described above, by adjusting the average particle diameter of the tetracalcium phosphate particles (A) to be larger that the average particle diameter of the calcium hydrogen phosphate particles (B), it is possible to achieve balance between solubilities of both of the materials and to maintain the pH of an aqueous solution at 8.5 to 9. This fact can cause hydroxyapatite crystals to form smoothly and also can improve the mechanical strength of a set product. Specifically, it is more preferable to adjust the average particle diameter of (A) to be not less than twice, even more preferably not less than four times, and particularly preferably not less than seven times the average particle diameter of (B). On the other hand, it is more preferable to adjust the average particle diameter of (A) to be not more than 35 times, even more preferably not more than 30 times, and particularly preferably not more than 25 times the average particle diameter of (B).

The inorganic particles (C) to be used in the present invention are at least one kind of particles selected from silica (silicon oxide) particles or titania (titanium oxide) particles, and particularly preferable as the inorganic particles (C) is silica. While the reason why a calcium phosphate composition from which a bone excellent in mechanical strength is formed and by which a high bone replacement rate is achieved can be obtained by using at least one kind of inorganic particles (C) selected from silica particles or titania particles in the present invention is not necessarily clear, it is expected that —OH groups, which are presumed to be present on the surface of silica particles or titania particles, serve for the formation of fine crystals of hydroxyapatite. For this reason, it is permissible to use silica particles or titania particles in which more hydroxyl groups have been introduced to the surface of the particles through treatment of silica particles or titania particles such as those described above with an aqueous solution of a strong base such as sodium hydroxide.

The average particle diameter of the inorganic particles (C) is from 0.002 to 0.5 μm. When the average particle diameter is less than 0.002 μm, the viscosity of the composition becomes so high that the handleability may deteriorate. The average particle diameter is more preferably 0.003 μm or more, and even more preferably 0.005 μm or more. On the other hand, when the average particle diameter is greater than 0.5 μm, the mechanical strength of formed bone may decrease, and the bone replacement rate also may decrease. Therefore, the average particle diameter is more preferably 0.2 μm or less, and even more preferably 0.1 μm or less. The average particle diameter of the inorganic particles (C) is calculated by observing primary particles dispersed in an epoxy resin using a transmission electron microscope.

The mixing ratio (A/B) of the tetracalcium phosphate particles (A) to the calcium hydrogen phosphate particles (B) is from 45/55 to 55/45 in molar ratio. Thereby, a calcium phosphate composition from which a bone excellent in mechanical strength is formed and by which a high bone replacement rate is achieved can be produced. It is optimal that the mixing ratio (A/B) is substantially 50/50.

The calcium phosphate composition of the present invention contains 0.1 to 20 parts by weight of the inorganic particles (C) based on 100 parts by weight in total of the tetracalcium phosphate particles (A) and the calcium hydrogen phosphate particles (B). When the content of the inorganic particles (C) is less than 0.1 part by weight, the bone replacement rate and the formed bone strength become almost equal to those achieved without the addition thereof, and almost no effect by the addition is recognized. The content of the inorganic particles (C) is preferably 0.2 part by weight or more, and more preferably 1 part by weight or more. On the other hand, when the content of the inorganic particles (C) is greater than 20 parts by weight, the bone replacement rate decreases and the formed bone strength after a lapse of a long time after implantation becomes low. The content of the inorganic particles (C) is preferably 15 parts by weight or less, and more preferably 10 parts by weight or less.

The calcium phosphate composition of the present invention may contain ingredients other than the tetracalcium phosphate particles (A), the calcium hydrogen phosphate particles (B) and at least one kind of inorganic particles (C) selected from silica particles or titania particles, unless the effect of the present invention is adversely affected. For example, a thickener may be incorporated according to need. This is for improving the moldability or uniform filling property of a calcium phosphate composition paste. The thickener may be, for example, one or two or more species selected from carboxymethylcellulose, sodium carboxymethylcellulose, hydroxypropylcellulose, hydroxypropylmethylcellulose, polyvinyl alcohol, polyethylene glycol, polyacrylic acid, polyglutamic acid, polyglutamic acid salts, polyaspartic acid, polyaspartic acid salts, starch other than cellulose, alginic acid, hyaluronic acid, polysaccharides such as pectin, chitin and chitosan, acidic polysaccharide esters such as propylene glycol alginate, and polymers such as proteins, e.g. collagen, gelatin and their derivatives. From aspects of solubility in water and viscosity preferred is at least one species chosen from sodium carboxymethylcellulose, hydroxypropylcellulose, hydroxypropylmethylcellulose, alginic acid, chitosan, polyglutamic acid and polyglutamic acid salts. The thickener may be incorporated into a calcium phosphate composition, or may be incorporated into a liquid material, or may be incorporated into a paste under mixing.

An X-ray contrast medium may also be contained according to need. This is because the operation of filling a calcium phosphate composition paste can be monitored or change of the paste after its filling can be traced. Examples of the X-ray contrast medium include one or two or more species selected from barium sulfate, bismuth subcarbonate, ytterbium fluoride, iodoform, barium apatite, barium titanate, etc. The X-ray contrast medium may be incorporated to a calcium phosphate composition, or incorporated to a liquid agent, or incorporated to a paste under mixing. The incorporated amount of the X-ray contrast medium used in the present invention is not particularly limited. However, considering the contrasting property, it is preferably from 5 to 30 parts by weight based on 100 parts by weight in total of the tetracalcium phosphate particles (A), calcium hydrogen phosphate particles (B) and inorganic particles (C). If the incorporated amount of the X-ray contrast medium is less than 5 parts by weight, the contrasting property may fail to be obtained. On the other hand, if the incorporated amount of the X-ray contrast medium is greater than 30 parts by weight, the mechanical strength of a set product of the calcium phosphate composition may decrease.

The calcium phosphate composition of the present invention may contain metal oxide particles other than silica particles or titania particles within the range in which the effect of the present invention is adversely affected. Specific examples of the metal oxide particles include alumina, zirconia, cerium oxide (ceria), hafnium oxide (hafnia), yttrium oxide (yttria), beryllium oxide (beryllia), niobium oxide (niobia), lanthanum oxide, bismuth oxide, tin oxide, zinc oxide, iron oxide, molybdenum oxide, nickel oxide, ytterbium oxide, samarium oxide, europium oxide, praseodymium oxide, magnesium oxide, and neodymium oxide.

Moreover, pharmacologically acceptable agents may be incorporated. For example, disinfectants, anticancer agents, antibiotics, antibacterial agents, blood circulation improvers such as actosin and PEG1, growth factors such as bFGF, PDGF and BMP, cells which promotes hard tissue formation, such as osteoblasts, odontoblasts, and anaplastic bone marrow derived stem cells may be incorporated.

While the calcium phosphate composition of the present invention is composed of the tetracalcium phosphate particles (A), the calcium hydrogen phosphate particles (B) and the at least one kind of inorganic particles (C) selected from silica particles or titania particles, the method of mixing thereof is not particularly restricted. For example, a container-driving mill such as a pestle and mortar machine and a ball mill, or a high speed rotation mill having a rotary blade on the bottom may be used. A high speed rotation mill is preferably used. It is also possible to mix in the presence of a water-free liquid agent such as alcohol.

The calcium phosphate composition of the present invention is sold as a powdery composition. At the time of using it at a medical site, the composition can be used by mixing with a liquid agent and then filling or applying it to a desired bone tissue. It is also permissible that the composition is sold in a paste form in which is dispersed in a dispersion medium such as alcohol and it is used as it is by filling or applying to a desired bone tissue at a medical site. In the latter case, it is set gradually with replacement of the dispersion medium by the water in the living body. In usual, it is often sold as a powdery composition. It is also possible to fill only a powdery composition to a bone tissue and then allow it to set using the moisture in the living body. A method in which a powdery composition is filled and then a liquid agent for setting is applied to the filled site in order to promote the setting is also used as a preferred embodiment. Moreover, also preferably performed is a method in which a calcium phosphate powder composition or a paste obtained by kneading it with a liquid agent is filled into a water-permeable mold, incubation is conducted under conditions including a temperature of 25° C. or higher and a relative humidity of 70% or higher to form a set product of the calcium phosphate composition, and the set product is implanted to a bone defect.

When the calcium phosphate composition of the present invention is a powdery composition, it is kneaded together with a liquid agent to yield a calcium phosphate composition paste at the time of being used at a medical site. The liquid agent to be used here may be pure water, an aqueous solution containing other ingredients dissolved therein, or an aqueous dispersion containing other ingredients dispersed therein. Examples of the ingredients to be incorporated to water include phosphoric acid, sodium salts of phosphoric acid such as disodium hydrogen phosphate and sodium dihydrogen phosphate, mixtures thereof, potassium salts of phosphoric acid, ammonium salts of phosphoric acid, pH buffers such as N,N-bis(2-hydroxyethyl)-2-aminoethanesulfonic acid, N-tris (hydroxymethyl)methyl-2-aminoethanesulfonic acid, fluoride salts such as sodium fluoride, potassium fluoride and ammonium fluoride, and water-soluble polyhydric alcohols such as glycerin and propylene glycol. In particular, it is preferable, to incorporate sodium salts of phosphoric acid such as disodium hydrogen phosphate and sodium dihydrogen phosphate, and mixtures thereof from the safety aspect.

It is also permissible to mix a liquid agent containing inorganic particles (C) not to a calcium phosphate composition composed of tetracalcium phosphate particles (A), calcium hydrogen phosphate particles (B) and inorganic particles (C), but to a powdery composition composed of tetracalcium phosphate particles (A) and calcium hydrogen phosphate particles (B). That is, it is also possible to provide a calcium phosphate composition paste by adding an aqueous dispersion in which 0.1 to 20 parts by weight, to 100 parts by weight in total of (A) and (B), of inorganic particles (C) are dispersed to a powder of a composition composed of tetracalcium phosphate particles (A) and calcium hydrogen phosphate particles (B), followed by kneading. Examples of a preferable aqueous dispersion in which (C) is dispersed include aqueous dispersions in which colloidal silica, colloidal titania or the like is dispersed.

While the mass ratio of a calcium phosphate composition to a liquid agent (calcium phosphate composition/liquid agent) in the preparation of the calcium phosphate composition is not particularly limited, it is preferably from 10/10 to 60/10, and more preferably from 25/10 to 45/10. The powdery composition and the liquid agent are kneaded well so that they can be mixed uniformly, and then they are filled or applied promptly to a bone tissue.

The calcium phosphate composition of the present invention is used for various medical applications. For example, it is preferably used as a bone cement for adhering or fixing. When the calcium phosphate composition of the present invention is used for this application, it can be filled to all parts with a complicated form because of excellent filling property of a paste. It is excellent in biocompatibility because the paste itself changes into hydroxyapatite within a short period of time in a living body or an oral cavity and it is replaced by a newly formed bone at a filled site, resulting in integration with a biological hard tissue.

EXAMPLES

The present invention is illustrated below more concretely with reference to Examples. In the Examples, regarding an average particle diameter of tetracalcium phosphate particles (A) and calcium hydrogen phosphate particles (B), measurement was conducted using a laser diffraction type particle size distribution analyzer ("SALD-2100" manufactured by Shimadzu Corporation), and a median diameter calculated from the result of the measurement was defined as the average particle diameter. An average particle diameter of inorganic particles (C) was measured as follows. To 5 g of an epoxy resin before setting which was prepared by the Luft method (Luft JH: Improvements in epoxy resin embedding methods, J Biophys Biochem Cytol, 9: 409-414, 1961.), 1 g of inorganic particles (C) were added, followed by stirring until becoming uniform and then by degassing under reduced pressure. Thereafter, the mixture was added to a BEEM capsule for setting (8 mm in inner diameter, 15 mm in height) and was set by incubation at 60° C. for 2 days. An ultrathin section obtained with an ultramicrotome ("SuperNova" manufactured by Reichert-Jung) from a part of the set product resulting from trimming of a top portion about 5 mm in length was observed with a transmission electron microscope ("H-9000UHR" manufactured by Hitachi, Ltd.). Thus, the particle diameter of the inorganic particles (C) was measured.

Example 1

(1) Preparation of Calcium Phosphate Composition

As the tetracalcium phosphate particles (A) for this experiment, commercially available tetracalcium phosphate particles (made by Taihei Chemical Industrial Co., Ltd., 8.75 μm in average particle diameter) were used. The anhydrous calcium hydrogen phosphate particles (B) for this experiment (1.14 μm in average particle diameter) were obtained by subjecting a slurry resulting from addition of 50 g of commercially available anhydrous calcium hydrogen phosphate particles (made by Taihei Chemical Industrial Co., Ltd., 10.12 μm in average particle diameter), 120 g of 95% ethanol ("Ethanol (95)" made by Wako Pure Chemical Industries, Ltd.) and 240 g of zirconia balls having a diameter of 10 mm into a 400-ml grinding pot made of alumina ("Type A-3 HD pot mill" manufactured by Nikkato Corp.) and subsequent wet grinding at a rotation speed of 120 rpm for 24 hours, to evaporation of ethanol with a rotary evaporator, followed by drying at 60° C. for 6 hours and additional vacuum drying at 60° C. for 24 hours. The tetracalcium phosphate particles (A) 72.9 g, the anhydrous calcium hydrogen phosphate particles (B) 27.1 g, and silica particles ("AEROSIL 300" made by Degussa Co., 0.007 μm in average particle diameter) 5 g, in 5 parts by weight to 100 parts in total of (A) and (B), were added into a high speed rotation mill ("SM-1" manufactured by As One Corp.), followed by mixing at a rotation blade speed of 3000 rpm for 3 minutes to yield a calcium phosphate composition. In this process, there was substantially no change in average particle diameter between before and after the mixing with the tetracalcium phosphate particles (A), the calcium hydrogen phosphate particles (B) and the silica particles. The resulting calcium phosphate composition was subjected to γ-ray sterilization (25 kGy) using cobalt 60 as a radiation source.

(2) Preparation of Calcium Phosphate Composition Paste

A calcium phosphate composition paste was prepared by precisely weighing out 1.5 g of the calcium phosphate composition obtained above, adding thereto 0.43 g of a 0.2 M aqueous $Na_2HPO_4$ solution, and kneading (the powder-to-liquid mixing weight ratio was 3.5). In this process, a liquid agent which had been sterilized with a filter was used and all the operations were conducted under sterilized conditions.

(3) Implantation of Calcium Phosphate Composition Paste

Male dogs having a matured skeleton (about 30 kg in weight) were used for this evaluation. An incision of 7-10 cm in length was formed in the skin near the tibia under anesthesia. The subcutaneous tissue and the underlying muscle were incised or the connective tissue was ablated, thereby exposing the periosteum. A cut was formed in this periosteum, and then the left tibia and the right tibia of an animal were each provided with a bone defect of 6 mm in diameter and 6 mm in depth using a drill. The size of the defects was the same among all the test animals, and the size actually measured was equal. The calcium phosphate composition paste prepared above was filled into the defects and then left at rest for about 10 minutes, followed by confirmation of its setting. Thereafter, the periosteum, the muscle and the skin were closed by suture. All the operations were conducted under sterilized conditions. Then, breeding was continued for a predetermined period.

(4) Measurement of Bone Replacement Rate

An animal after a lapse of 3 months from the treatment was euthanized by endocardial overdosage injection of 150 mg/kg of pentobarbital. The tibial bone tissue was taken and cut, and thereby a bone tissue of about 2 cm in length, about 2 cm in width and about 1 cm in depth including an implantation site was taken. The bone tissue obtained above was fixed in 10 vol % neutral buffered formalin, and then the tissue was embedded in a resin. Thus, a 10 μm-thick section of the central portion of the implantation site in a direction perpendicular to the longitudinal direction of the bone was prepared. After removal of the resin, the section was subjected to Hematoxylin and Eosin staining. A tissue image of the section was captured from a CCD camera, and the area of autologous bone, observed as an osteoid tissue, by which the calcium phosphate composition had been replaced, and the area of an implanted calcium phosphate composition observed as a non-living-body-tissue-like uniform artifact were each measured with an image analyzer ("LUZEX D QJ8075, 1" manufactured by NIRECO Corp.). Thereby, the bone replacement rate of each calcium phosphate composition was measured. Five visual fields in each of two different sections of an implanted animal were observed in the same manner as above, and then the average of the bone replacement rates of the ten visual fields was calculated. In Example 1, the bone replacement rate was 61%.

(5) Flexural Strength of Bone Tissue at Calcium Phosphate Composition-Implanted Site An animal after a lapse of 3 months from the treatment and an animal after a lapse of 6 months from the treatment were euthanized by endocardial overdosage injection of 150 mg/kg of pentobarbital. A tibial bone tissue containing the implanted site was taken and fixed in 10% neutral buffered formalin. Then, it was cut so that the center of the implanted site became the center of a specimen, and thereby a bone specimen for flexural strength measurement was prepared which was long in the longitudinal direction of the bone and of 32 mm in length, 2 mm in width and 2 mm in height. The specimen was measured for flexural strength (n=5) using a mechanical strength analyzer ("AG-I 100 kN" manufactured by Shimadzu Corp.) under conditions including a span of 20 mm, a central concentration loading method, and a loading rate of 1 mm/min in accordance with ASTM F417-78 (Standard test method for flexural strength of electrical grade ceramics). The flexural strength of the implanted-site bone tissue at the third month and that of the implanted-site bone tissue at the sixth month were 99.4±5.8 MPa and 93.9±7.2 MPa, respectively.

Examples 2 and 3

Preparation and evaluation of a calcium phosphate composition were conducted in the same manner as Example 1, except for changing the content of the silica particles ("AEROSIL 300" made by Degussa Co., 0.007 μm in average particle diameter) in Example 1 to 0.2 part by weight (Example 2) and 15 parts by weight (Example 3), respectively. The results obtained are summarized in Table 1.

Example 4

Preparation and evaluation of a calcium phosphate composition were conducted in the same manner as Example 1, except for using 5 parts by weight of titania particles ("Titanium Dioxide P25" made by Degussa Co., 0.021 pin in average particle diameter) instead of the silica particles ("AEROSIL 300") in Example 1. The results obtained are summarized in Table 1.

Comparative Example 1

Preparation and evaluation of a calcium phosphate composition were conducted in the same manner as Example 1, except for adding no silica particles ("AEROSIL 300") in Example 1. The results obtained are summarized in Table 1.

Comparative Example 2

Preparation and evaluation of a calcium phosphate composition were conducted in the same manner as Example 1, except for using, instead of the silica particles ("AEROSIL 300") in Example 1, silica particles ("CARPLEX FPS-4" made by Shionogi & Co., Ltd., 2.3 μm in average particle diameter) differing from "AEROSIL 300" in particle size. The results obtained are summarized in Table 1.

Comparative Examples 3 and 4

Preparation and evaluation of a calcium phosphate composition were conducted in the same manner as Example 1, except for changing the content of the silica particles ("AEROSIL 300") in Example 1 to 0.05 part by weight (Comparative Example 3) and 25 parts by weight (Comparative Example 4), respectively. The results obtained are summarized in Table 1.

Comparative Examples 5 and 6

Preparation and evaluation of a calcium phosphate composition were conducted in the same manner as Example 1, except for using the inorganic fine particles given below each in 5 parts by weight instead of the silica particles ("AEROSIL 300") in Example 1. The results obtained are summarized in Table 1.

Comparative Example 5

Alumina Particles ("Aluminum Oxide C" made by Degussa Co., 0.013 μm in average particle diameter)

Comparative Example 6

Zirconia Particles (Prototype made by Degussa Co., 0.030 μm in average particle diameter)

Comparative Example 7

Preparation and evaluation of a calcium phosphate composition were conducted in the same manner as Example 1, except for changing the molar ratio (A/B) of the tetracalcium phosphate particles (A) to the anhydrous sodium dihydrogen phosphate particles (B) in Example 1 to 0.7. The results obtained are summarized in Table 1.

were used, formed bone strength was inferior to a case of using silica particles (Example 1), further third-month formed bone strength was greatly inferior in particular. In Comparative Example 7, in which the molar ratio (A/B) of tetracalcium phosphate particles (A) to anhydrous calcium hydrogen phosphate particles (B) was adjusted to 0.7, decrease in formed bone strength was recognized in comparison to Example 1, in which the molar ratio (A/B) was 1.0.

In Example 2, in which the content of silica particles was 0.2 part by weight, decrease in both bone replacement rate and formed bone strength was recognized in comparison to the case where the content was 5 parts by weight (Example 1). In contrast to this, in Example 3, in which the content of silica particles was 15 parts by weight, the bone replacement rate was almost equal to that in the case where the content was 5

TABLE 1

| | Inorganic particle (C) | | | TTCP/ DCPA (*1) (mol/ mol) | Average bone replacement rate (3 months, %) | Flexural strength of bone tissue in implanted part (3 months, MPa) | Flexural strength of bone tissue in implanted part (6 months, MPa) |
|---|---|---|---|---|---|---|---|
| | Kind | Particle diameter (μm) | Blended amount (part by weight) | | | | |
| Example 1 | Silica | 0.007 | 5 | 1 | 61 | 99.4 ± 5.8 | 93.9 ± 7.2 |
| Example 2 | Silica | 0.007 | 0.2 | 1 | 42 | 58.7 ± 2.3 | 87.0 ± 5.3 |
| Example 3 | Silica | 0.007 | 15 | 1 | 62 | 84.4 ± 6.6 | 87.2 ± 4.1 |
| Example 4 | Titania | 0.021 | 5 | 1 | 59 | 80.9 ± 3.5 | 90.9 ± 3.9 |
| Comparative Example 1 | — | — | — | 1 | 30 | 28.1 ± 0.6 | 50.4 ± 0.9 |
| Comparative Example 2 | Silica | 2.3 | 5 | 1 | 37 | 23.7 ± 0.4 | 29.8 ± 0.5 |
| Comparative Example 3 | Silica | 0.007 | 0.05 | 1 | 31 | 29.6 ± 0.6 | 51.3 ± 0.4 |
| Comparative Example 4 | Silica | 0.007 | 25 | 1 | 41 | 57.3 ± 0.9 | 50.3 ± 0.6 |
| Comparative Example 5 | Alumina | 0.013 | 5 | 1 | 55 | 55.6 ± 7.5 | 92.4 ± 5.8 |
| Comparative Example 6 | Zirconia | 0.030 | 5 | 1 | 59 | 57.9 ± 2.1 | 86.0 ± 7.8 |
| Comparative Example 7 | Silica | 0.007 | 5 | 0.7 | 45 | 48.0 ± 0.8 | 67.8 ± 4.9 |

(*1) TTCP: Tetracalcium phosphate particle DCPA: Anhydrous calcium hydrogen phosphate particle As is clear from Table 1, in Examples 1 to 4, in which calcium phosphate compositions comprising tetracalcium phosphate particles (A), calcium hydrogen phosphate particles (B) and inorganic particles (C) were used, greater improvement in bone replacement rate and in formed bone strength was recognized in comparison to Comparative Example 1, in which a calcium phosphate composition composed only of tetracalcium phosphate particles (A) and calcium hydrogen phosphate particles (B) was used. This fact clearly shows the effect caused by addition of the inorganic particles (C).

In Comparative Example 2, in which silica particles having an average particle diameter of larger than 0.5 μm were added, both of the bone replacement rate and the formed bone strength were greatly inferior to Examples. In Comparative Example 3, in which the content of silica particles was less than 0.1 part by weight, both of the bone replacement rate and the formed bone strength were greatly inferior to Examples. Comparative Example 4, in which the content of silica particles was more than 20 parts by weight, did not differ from Examples 1 to 4 much in third-month formed bone strength, but it was greatly inferior to Examples 1 to 4 in both bone replacement rate and sixth-month formed bone strength. In Comparative Example 5, in which alumina particles were used, and Comparative Example 6, in which zirconia particles parts by weight (Example 1), but decrease in both third-month formed bone strength and sixth-month formed bone strength was recognized. In Example 4, in which titania particles were used, satisfactory bone replacement rate and formed bone strength were achieved, but the performance was slightly inferior to that in the case where silica particles were used (Example 1).

The invention claimed is:

1. A powdered calcium phosphate composition comprising:
    tetracalcium phosphate particles (A),
    calcium hydrogen phosphate particles (B), and
    at least one kind of inorganic particles (C) selected from silica particles or titania particles,
    wherein the mixing ratio (A/B) of (A) to (B) is from 45/55 to 55/45 in molar ratio, the inorganic particles (C) have an average particle diameter of from 0.002 to 0.021 μm, and the inorganic particles (C) are contained in an amount of 0.1 to 20 parts by weight based on 100 parts by weight of (A) and (B) in total.

2. The powdered calcium phosphate composition according to claim 1, wherein the tetracalcium phosphate particles (A) have an average particle diameter of from 5 to 30 μm.

3. The powdered calcium phosphate composition according to claim 1, wherein the calcium hydrogen phosphate particles (B) have an average particle diameter of from 0.1 to 5 µm.

4. A method for producing a calcium phosphate composition paste comprising tetracalcium phosphate particles (A), calcium hydrogen phosphate particles (B) and at least one kind of inorganic particles (C) selected from silica particles or titania particles, the method comprising:

adding an aqueous solution or a buffered aqueous solution to a powder of a calcium phosphate composition in which the mixing ratio (A/B) of (A) to (B) is from 45/55 to 55/45 in molar ratio, the inorganic particles (C) have an average particle diameter of from 0.002 to 0.021 µm, and the inorganic particles (C) are contained in an amount of 0.1 to 20 parts by weight based on 100 parts by weight of (A) and (B) in total; and kneading the resulting mixture.

5. A composition suitable for medical use comprising the powdered calcium phosphate composition according to claim 1; and at least one pharmacologically acceptable agent.

6. A bone cement comprising the powdered calcium phosphate composition according to claim 1.

7. A composition suitable for medical use comprising the powdered calcium phosphate composition according to claim 2; and at least one pharmacologically acceptable agent.

8. A bone cement comprising the powdered calcium phosphate composition according to claim 2.

9. A composition suitable for medical use comprising the powdered calcium phosphate composition according to claim 3; and at least one pharmacologically acceptable agent.

* * * * *